US010258746B2

(12) United States Patent
Radmand et al.

(10) Patent No.: US 10,258,746 B2
(45) Date of Patent: Apr. 16, 2019

(54) APPARATUS AND METHOD OF AUTOMATICALLY REMOVING A NEEDLE FROM A HUB (71) Applicant: Inventive Medical Devices, LLC, Stratford, CT (US)

(72) Inventors: Reza Radmand, Brookline, MA (US); Ali Moghadam, Trumbull, CT (US)

(73) Assignee: Inventive Medical Devices, LLC, Stratford, CT (US)

( * ) Notice: Subject to any disclaimer, the term of this patent is extended or adjusted under 35 U.S.C. 154(b) by 126 days.

(21) Appl. No.: 15/129,405

(22) PCT Filed: Mar. 19, 2015

(86) PCT No.: PCT/US2015/021450
§ 371 (c)(1),
(2) Date: Sep. 26, 2016

(87) PCT Pub. No.: WO2015/148257
PCT Pub. Date: Oct. 1, 2015

(65) Prior Publication Data
US 2017/0173272 A1    Jun. 22, 2017

Related U.S. Application Data (60) Provisional application No. 61/970,079, filed on Mar. 25, 2014.

(51) Int. Cl.
*A61M 5/32* (2006.01)
*B23P 19/04* (2006.01)
*A61B 50/30* (2016.01)

(52) U.S. Cl.
CPC ....... *A61M 5/3276* (2013.01); *A61B 50/3001* (2016.02); *A61M 5/3213* (2013.01);
(Continued)

(58) Field of Classification Search
CPC .............. A61M 5/3276; A61M 5/3213; A61M 2205/14; A61B 50/3001; B23P 19/04;
(Continued)

(56) References Cited

U.S. PATENT DOCUMENTS 3,921,841 A    11/1975  Mizutani et al.
4,801,013 A     1/1989  Bruno
(Continued)

FOREIGN PATENT DOCUMENTS

CA    2781364 A1 *  12/2012  .......... A61M 5/3205
EP    0838228 A2     4/1998
EP    2596825 A1     5/2013

OTHER PUBLICATIONS

International Search Report and Written Opinion of International Application No. PCT/US2015/021450, dated Aug. 12, 2016.
(Continued)

Primary Examiner — Jermie Cozart
(74) Attorney, Agent, or Firm — Moyles IP, LLC (57) ABSTRACT An apparatus and method of automatically and safely removing a needle from a syringe assembly while retaining a syringe hub as part of the syringe assembly is generally described. A needle containment device is provided, which may include a needle handling apparatus and a shutter mechanism assembly. The needle handling apparatus is configured for receiving at least a portion of a syringe assembly including at least a needle and a syringe hub, wherein a first clamping mechanism is configured to clamp the syringe hub and a second clamping mechanism is configured to clamp the needle, so that the needle is safely and automatically removed from the syringe hub.

19 Claims, 12 Drawing Sheets (52) U.S. Cl.
CPC ...... *B23P 19/04* (2013.01); *A61M 2005/3215* (2013.01); *A61M 2205/14* (2013.01); *Y10T 29/49822* (2015.01); *Y10T 29/53039* (2015.01); *Y10T 29/53061* (2015.01); *Y10T 29/53443* (2015.01)

(58) Field of Classification Search
CPC ......... Y10T 29/53443; Y10T 29/49822; Y10T 29/53061; Y10T 29/53039; Y10T 29/53339
See application file for complete search history.

(56) References Cited

U.S. PATENT DOCUMENTS

| | | | |
|---|---|---|---|
| 4,867,309 A | 9/1989 | Germain | |
| 4,950,015 A | 8/1990 | Nejib et al. | |
| 4,986,811 A | 1/1991 | Thead et al. | |
| 5,275,280 A | 1/1994 | Everhart | |
| 5,351,381 A * | 10/1994 | Case | A61M 5/3278 29/282 |
| 5,482,207 A | 1/1996 | Nelson et al. | |
| 5,761,975 A | 6/1998 | Waluda | |
| 5,791,471 A | 8/1998 | Radmand | |
| 5,947,950 A * | 9/1999 | Shillington | A61M 5/3205 206/366 |
| 6,117,110 A | 9/2000 | Radmand | |
| 6,202,843 B1 * | 3/2001 | Kelson | A61M 5/3205 206/366 |
| 7,850,646 B2 | 12/2010 | Segal | |
| 7,971,715 B1 | 7/2011 | Fernandes et al. | |
| 8,201,323 B2 | 6/2012 | Miller et al. | |
| 9,011,385 B2 * | 4/2015 | Bianco | A61M 5/3205 604/178 |
| 2003/0029014 A1 * | 2/2003 | Samuel | A61M 5/3205 29/426.4 |
| 2005/0012478 A1 * | 1/2005 | Cooley | A61M 5/3205 318/139 |
| 2005/0288636 A1 * | 12/2005 | Gerald Cooley | A61M 5/3205 604/187 |
| 2010/0106135 A1 | 4/2010 | Radmand | |
| 2012/0145577 A1 | 6/2012 | Bode | |
| 2013/0012886 A1 * | 1/2013 | Kawachi | A61M 5/3202 604/192 |
| 2013/0150804 A1 | 6/2013 | Bianco et al. | |
| 2015/0297838 A1 | 10/2015 | Steel et al. | |
| 2017/0173272 A1 | 6/2017 | Radmand et al. | |

OTHER PUBLICATIONS

Safepoint, Automatic and safe needle disposal, The Probe, Oct. 2011, p. 48.
Sharpsfree, SMS—Personal Syringe Management System for Home Use, Product Summary Sheet.
Dentsply, Jenker (TM) Needle Recapper—Needlestick Protector—Needle Recapper—Dentsply Professional.
International Search Report and Written Opinion of International App. No. PCT/US2018/055114, dated Jan. 3, 2019, relevant to U.S. Appl. No. 15/129,405, 14 pgs.

* cited by examiner

APPARATUS AND METHOD OF AUTOMATICALLY REMOVING A NEEDLE FROM A HUB

CROSS-REFERENCE TO RELATED APPLICATIONS

This application claims priority to PCT Application No. PCT/US2015/021450 filed Mar. 19, 2015, which claims the benefit of U.S. Provisional Application No. 61/970,079, filed filed Mar. 25, 2014, each of which is incorporated herein by reference in its entirety.

FIELD

An apparatus and method of automatically and safely removing a needle from a syringe assembly while retaining a hub as part of the syringe assembly is generally described.

BACKGROUND

As is commonly known by those of ordinary skill in the art, maintaining safety of healthcare personnel who handle needles in a healthcare setting is an ongoing problem.

Figure 1:
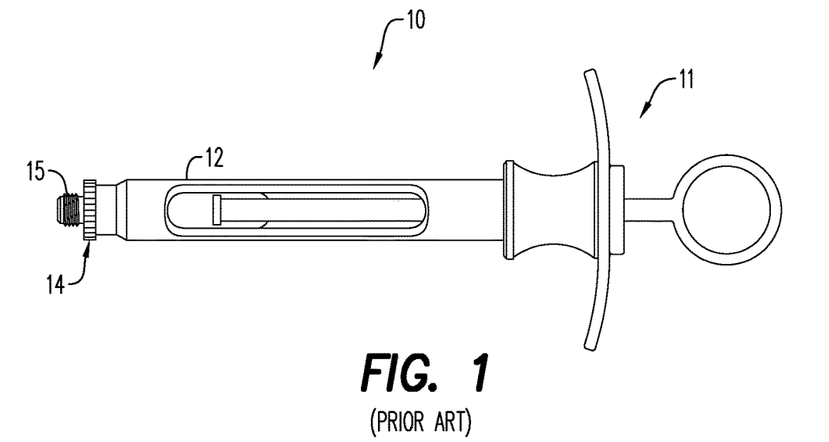
FIG. 1 is a side perspective view of a prior art syringe assembly.
Figure 2:
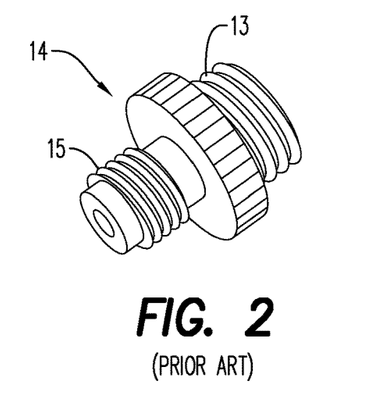
FIG. 2 is an exploded perspective view of a syringe hub useful as part of the syringe assembly of FIG. 1.
Figure 3:
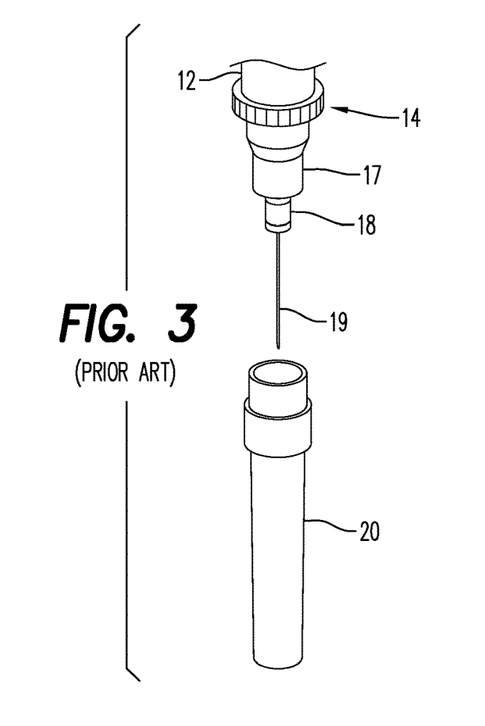
FIG. 3 is an exploded perspective view of a needle assembly useful as part of the syringe assembly of FIG. 1.

In particular, in dentistry, it is common for a dentist to use a syringe assembly 10 (see, for instance, FIGS. 1-3), for the purpose of injecting an anesthetic agent to patients before beginning and/or during a dental procedure. The syringe assembly 10 typically includes a handle 11, a syringe body 12, which receives a cartridge containing the anesthetic agent, and a hollow needle 16. In operation, upon depression of the handle 11, the dental anesthetic agent is pushed by a plunger moving through the cartridge (not shown) through the needle 16 into the patient. At the end of the syringe assembly 10 opposite the handle 11, is a syringe hub 14, which forms part of the syringe assembly 10, and for which the needle 16 is attached. The syringe hub 14 typically provides for a threaded attachment to the syringe assembly 10 at a syringe end 13 of the hub 14 and a threaded attachment to the needle 16 at a needle end 15 of the hub 14. With particular reference to FIG. 3, the syringe assembly 10 includes the syringe hub 14 attached at the syringe end 13 of the hub (see FIG. 2), and also attached to a cartridge end 17 of the needle assembly, a needle hub 18, the needle 16, an injection end 19 of the needle, which typically includes a beveled end, and a needle cap 20, (typically a plastic housing), for covering the needle 16 to maintain sterility of the needle 16, and also to prevent inadvertent sticks of the needle 16 into the patient and/or the healthcare personnel. As would be understood by one of ordinary skill in the art, the needle cap 20 is typically friction fit to remain in place as part of the syringe assembly 10 upon movement of the assembly, and thus prevent inadvertent exposure of the needle 16.

While there have been many attempts to provide for safe automatic removal of a needle from a syringe assembly, there has not been a device and method designed to retain the syringe hub with the syringe assembly, which has led to inadvertent disposal of this portion of the syringe assembly, leading to ensuing hazards associated with digging around in disposable sharps containers in an attempt to retrieve the syringe hub once it has been inadvertently disposed.

There also remains a need for a device and method that is capable of safely holding a syringe assembly between a first injection and completion of the dental procedure in case the healthcare personnel, e.g. the dentist, wishes to re-use the needle to supplement anesthesia dosing.

BRIEF DESCRIPTION

An apparatus and method of automatically and safely removing a needle from a syringe assembly while retaining a syringe hub as part of the syringe assembly is generally described.

A needle containment device is generally provided, which may include a needle handling apparatus and a shutter mechanism assembly. The needle handling apparatus is configured for receiving at least a portion of a syringe assembly including at least a needle and a syringe hub, wherein a first clamping mechanism is configured to clamp the syringe hub and a second clamping mechanism is configured to clamp the needle, and the needle is safely and automatically removed from the syringe hub. Further described is a removable protective sleeve for use with a needle containment device (or needle protection device) as described herein.

BRIEF DESCRIPTION OF THE FIGURES

A more particular description will be rendered by reference to specific embodiments thereof that are illustrated in the appended drawings. Understanding that these drawings depict only typical embodiments and are not therefore to be considered to be limiting of its scope, exemplary embodiments will be described and explained with additional specificity and detail through the use of the accompanying drawings in which.

Various features, aspects, and advantages of the embodiments will become more apparent from the following detailed description, along with the accompanying figures in which like numerals represent like components throughout the figures and text. The various described features are not necessarily drawn to scale, but are drawn to emphasize specific features relevant to some embodiments.

DETAILED DESCRIPTION

Reference will now be made in detail to various embodiments. Each example is provided by way of explanation, and is not meant as a limitation and does not constitute a definition of all possible embodiments.

Figure 4:
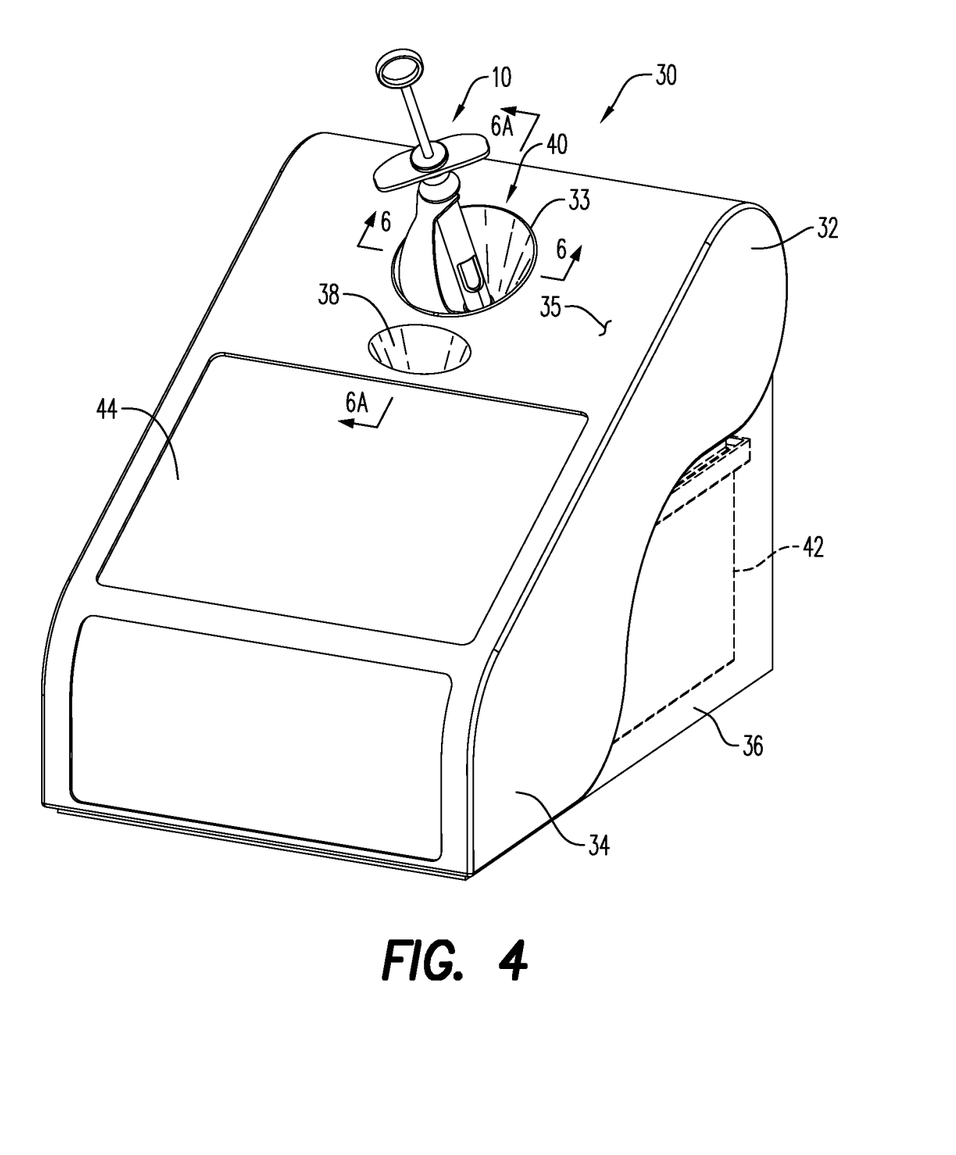
FIG. 4 is a perspective view of a needle containment device according to an embodiment.
Figure 5:
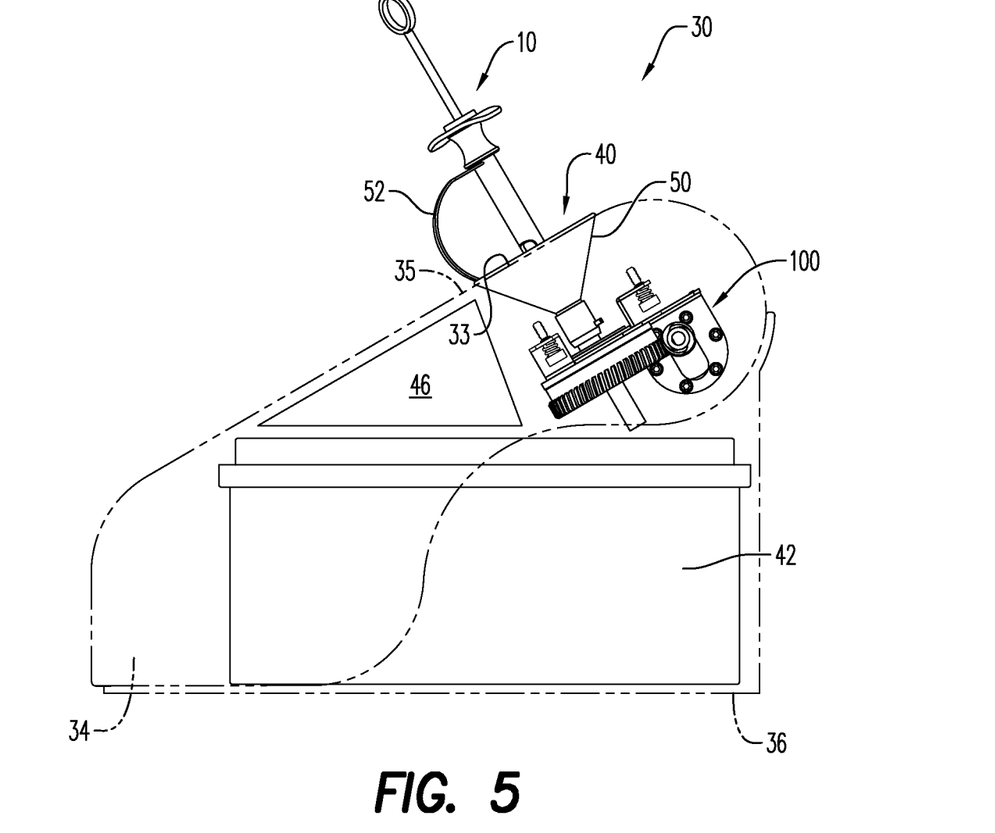
FIG. 5 is a side perspective view of the needle containment device of FIG. 4 according to an embodiment, illustrating components below a somewhat phantom housing cover and base.
Figure 14:
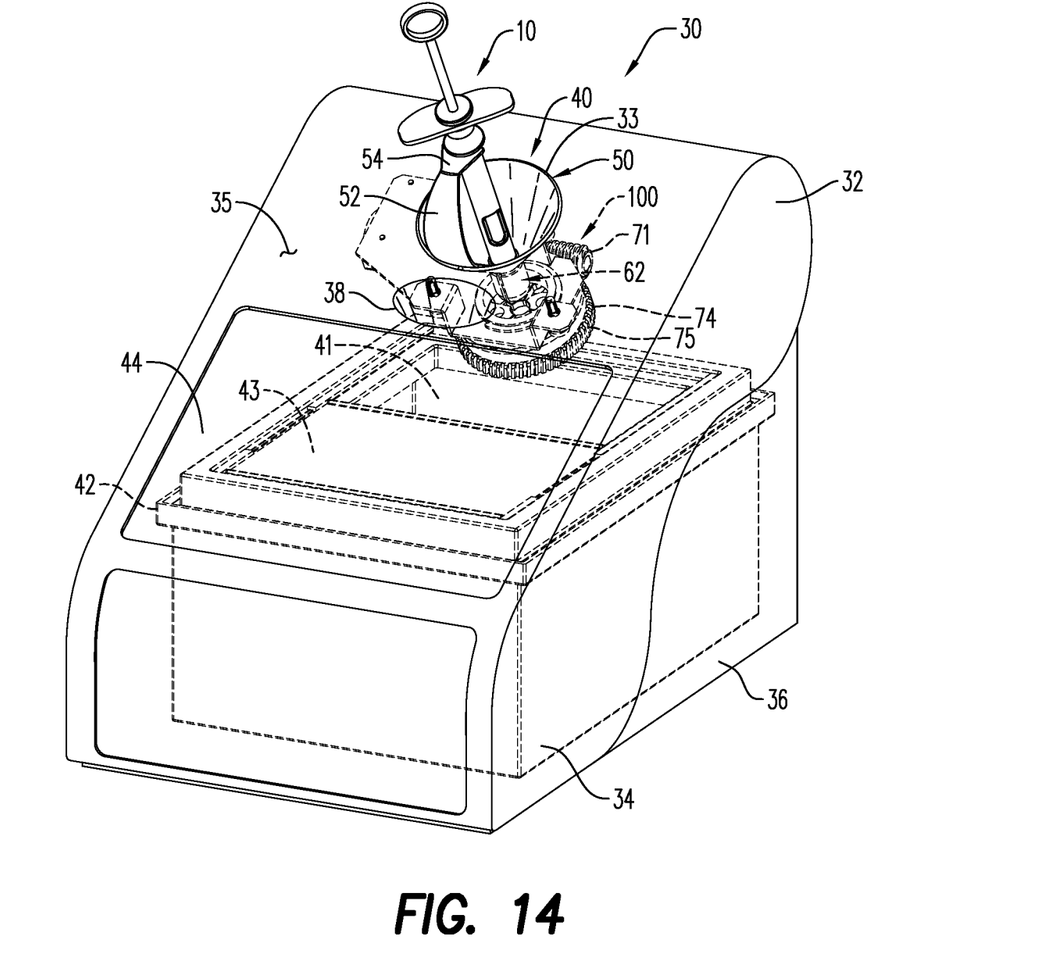
FIG. 14 is perspective view of the needle containment device of FIG. 4 in phantom.

For purposes of illustrating features of the embodiments, an example will now be introduced and referenced throughout the disclosure. Those skilled in the art will recognize that this example is illustrative and not limiting and is provided purely for explanatory purposes. In the illustrative example and as seen in FIGS. 4, 5 and 14, a reusable needle containment device 30 includes at least the following components: a housing 32, which typically includes at least a housing cover 34 and a housing base 36, a sharps slot 38, a control panel 44, and a housing opening 33 to receive a needle handling apparatus 40. In an embodiment, the housing cover 34 is hingedly attached to the housing base 36 to facilitate easy access to components housed within the housing 32 as discussed in greater detail below. As shown herein, the syringe assembly 10 is positioned in a seated position within the needle handling apparatus 40.

The control panel 44, is typically situated on an external or upper surface 35 of the housing 32, typically on the housing cover 34. The control panel 44 would typically include various indicators and/or switches configured to operate and/or display an indication of an automatic operation of the needle containment device 30, and more specifically, the needle handling apparatus 40 as described in greater detail below. In an embodiment, adjacent to or in close proximity to the control panel is a compartment 46 for housing a battery and electronic componentry (not shown).

Figure 9:
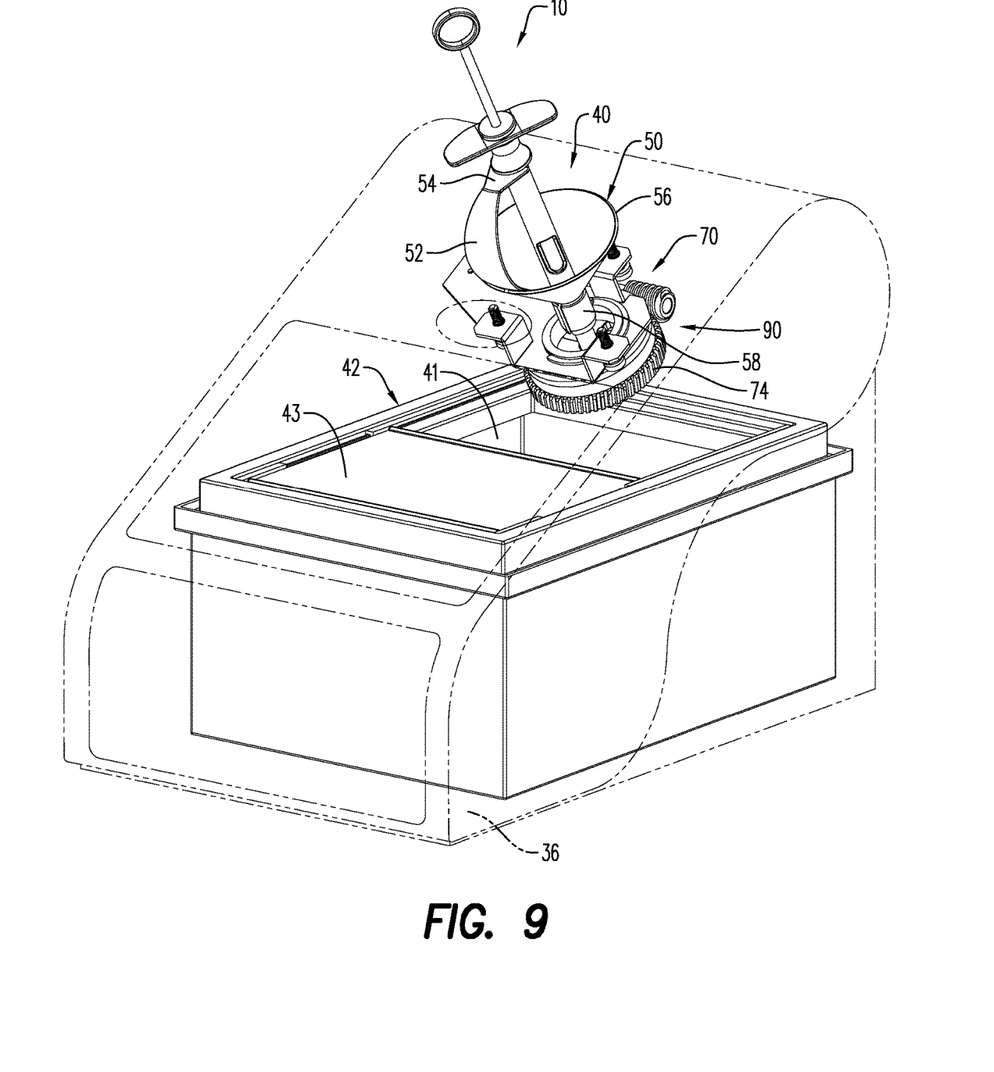
FIG. 9 is a perspective view of the needle containment device of FIG. 4 according to an embodiment, illustrating positioning of the needle handling apparatus without illustrating the housing cover and positioning of a removable sharps container in a somewhat phantom housing base.

Positioned within the housing 32 is a removable sharps container 42 that provides a receptacle for safe disposal of needles, syringes, lancets, razors and other sharp objects. The sharps container 42 is positioned in proximity to the needle handling apparatus 40 such that when the needle 16 is removed from the syringe hub 14, the needle 16 falls into, is released into or is otherwise deposited into the removable sharps container 42 for later disposal. Similarly, the sharps slot 38 is sized and positioned in the housing 32 to receive other items suitable for disposal in the sharps container 42. As depicted in FIGS. 5 and 9, the needle handling apparatus 40 is positioned such that when the needle 16 and/or needle cap or guard 20 are automatically and successfully removed from the syringe assembly 10, it simply drops into a slot or opening 41 formed in an upper surface 43 of the removable sharps container 42. While not shown in detail, a sensor 45 may be provided to a detect a capacity level of needles 16 and/or caps 20 within the sharps container 42, and a digital indicator may be provided to indicate, typically in the form of visual and/or audible indicators through components on the control panel 44, the capacity level. In an embodiment, if the sensor 45 detects the level and sends a signal to the indicator that the sharps container 42 has reached capacity, e.g., 75% full beyond safe level, then a bar graph LED may visually display the level and/or the audible alarm may be activated. In an embodiment, the electronic componentry housed in compartment 46 will disable operation of the needle handling apparatus 40 when the alarm is activated.

In an embodiment, an additional sensor is provided (not shown) to detect when at least a portion of the syringe assembly 10, e.g. the needle 16 and/or needle cap 20, has been inserted into the needle handling apparatus 40, and to trigger automatic clamping of the needle 16 and/or needle cap 20 in an initial step of removing the needle 16 and/or needle cap 20 from the syringe assembly 10. In an embodiment, the needle containment device 30 automatically detects insertion of the needle 16 and/or needle cap 20 into the needle containment device 30 and in response to automatically detecting the insertion, automatically activates removal of the needle 16 and/or needle cap 20 from the syringe hub 14. In an embodiment (not shown), the detection occurs through use of, for instance, one or motion detection lasers positioned along a path/movement traveled by the needle 16 and/or needle cap 20, such that when the motion is detected, automatic initiation of the removal process may begin.

Figure 6:
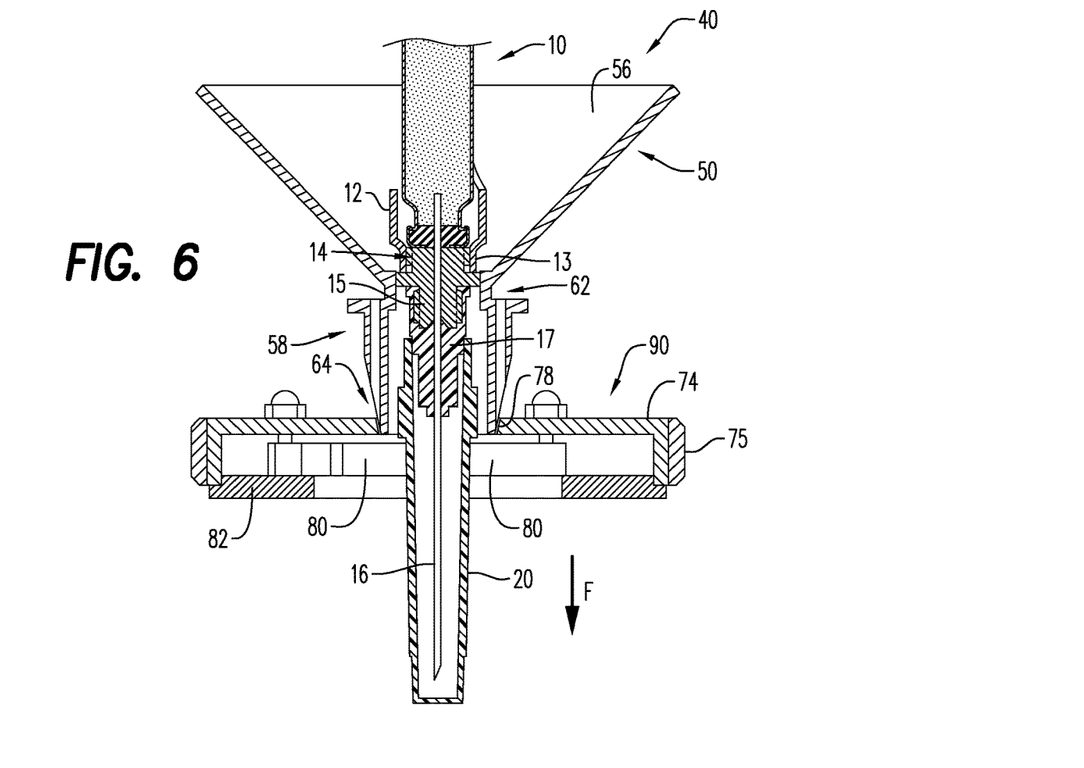
FIG. 6 is a cross-sectional view of a needle handling apparatus of FIG. 4 according to an embodiment.

In the illustrative example and as seen in FIG. 6, a needle 16 end of a syringe assembly 10 is inserted into a needle handling apparatus 40 of the needle containment device 30 (FIGS. 4-5). The needle handling apparatus 40 includes a removable protective sleeve/funnel/cup 50, (FIGS. 5-11 and 14), that is configured to receive at least a portion of the syringe assembly 10, to hold the syringe assembly 10 during one or more re-capping events, and to provide a first clamping mechanism or neck portion 62 to facilitate removal of the needle 16 and/or the needle cap 20 while retaining the syringe hub 14. In other words, the syringe hub 14 remains attached to the syringe assembly 10. In an embodiment, the removable protective sleeve 50 is made from a sterilizable material for multiple re-uses, and in another embodiment is disposable.

Figure 7:
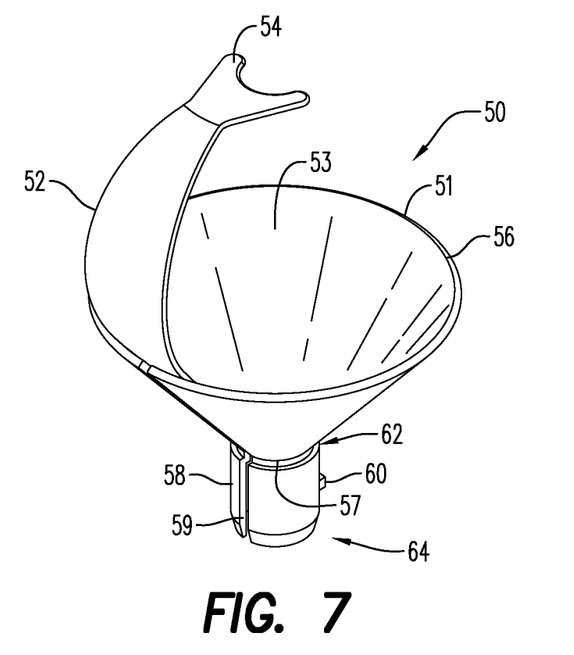
FIG. 7 is a perspective view a removable protective sleeve according to an embodiment.
Figure 8:
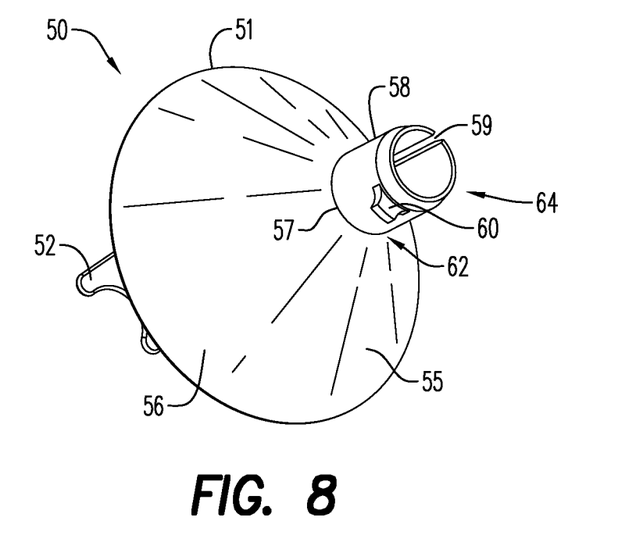
FIG. 8 is a perspective view of the opposite end of the removable protective sleeve of FIG. 7.

With reference to FIGS. 7 and 8 and in an embodiment, the removable protective sleeve 50 includes a sleeve body 56 that takes the shape of a funnel sloping inwardly from a peripheral edge 51 to a base or bottom 57, and wherein the shape is particularly adapted to guide the syringe assembly 10 (see, for instance, FIGS. 9 and 10) towards a channel 58 formed at and extending from the base 57 of the body 56. FIG. 7 depicts an inner surface 53 of the body 56 of the sleeve 50, while FIG. 8 depicts the sleeve 50 of FIG. 7 tilted to show an outer surface 55 of the body 56. In an embodiment, the channel 58 includes a slotted opening 59 along its length or at least a portion of its length, the slotted opening 59 extending from the end of the channel 58 that attaches to the base 57 of the sleeve 50, to its opposite end. Further, the channel 58 is made from a resilient material, meaning that the channel 58 can be at least partially closed by, for instance, pinching the channel 58 to close the slotted opening 59, but for which the channel 58 can be returned to its original shape upon removal of the pinching force.

Figure 10:
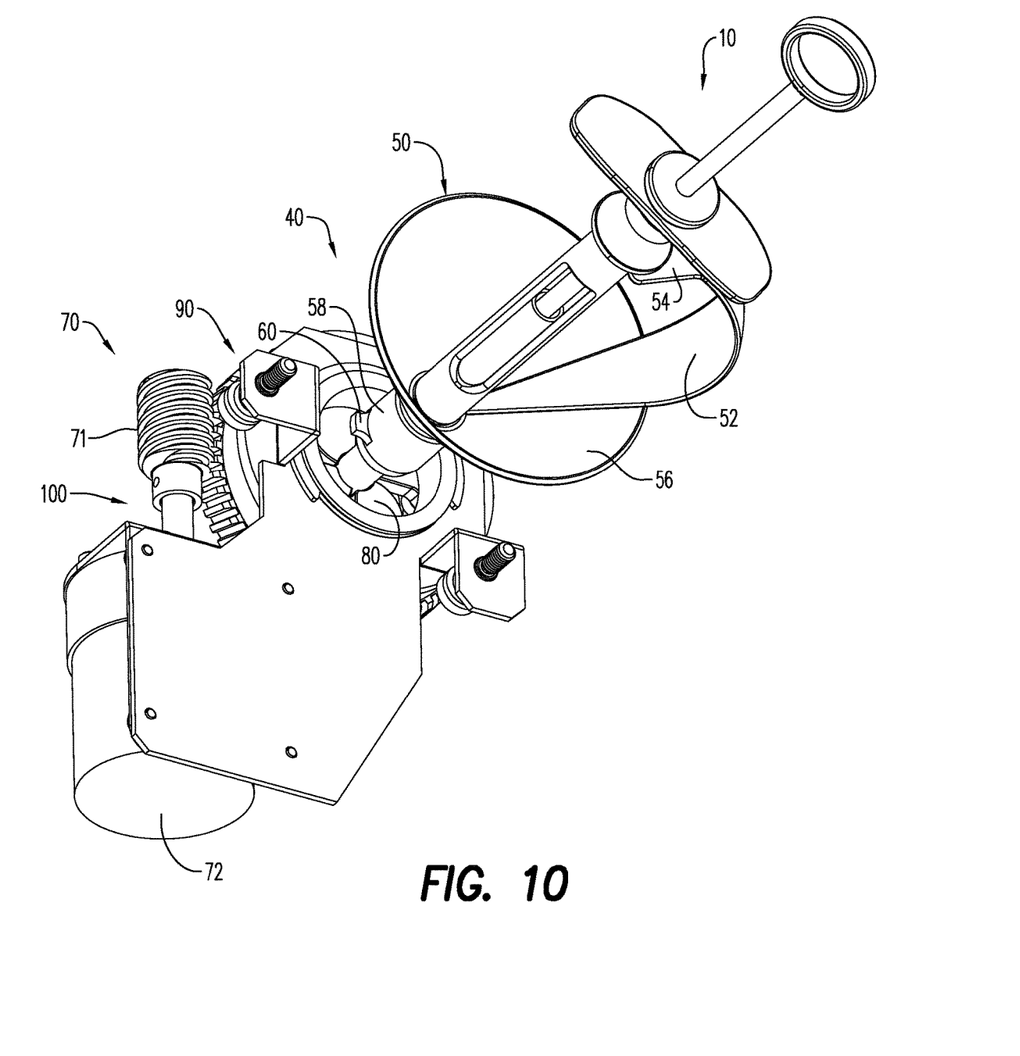
FIG. 10 is a perspective view of the needle handling apparatus according to an embodiment.

A syringe supporting arm 52 extends from the body 56, in an embodiment, typically from the peripheral edge 51 of the sleeve 50 and is configured to support at least a portion of the syringe assembly 10. As depicted in FIG. 10, the supporting arm 52 extends along an entire inner surface 53 of the body 56 of the sleeve 50, and may be used together with a weld, rivet or other attachment means to form the funnel shape by joining ends of the body 56 (not shown). With reference again to FIG. 7, extending from the end of the supporting arm 52, opposite to the end of the supporting arm 52 extending from the peripheral edge 51 of the sleeve 50, is a support arm end 54. In an embodiment, the supporting arm 52 is a curved, rigid structure of sufficient substance to support the syringe assembly 10 when the needle 16 is positioned within the channel 58, and the support arm end 54 includes structure adapted to receive the body 12 of the syringe assembly 10. For instance, and as shown in FIG. 7, the support arm end 52 includes a slotted portion in the shape of two fingers that is configured to support the syringe body 12 whilst the syringe assembly 10 is supported by and positioned within the needle handling apparatus 40.

Turning to FIGS. 11-14, the needle handling apparatus 40 further includes a second clamping mechanism 70. The second clamping mechanism 70 generally includes a shutter mechanism assembly 90 and a motor/gear assembly 100 (see, for instance, FIG. 11). As depicted, for instance, in FIG. 11, the motor/gear assembly 100 includes a motor 72, with a gear 71, typically a screw-type worm gear 73, extending therefrom for mating engagement with and activation (e.g. rotation) of the second clamping mechanism 70. In an embodiment, the motor/gear assembly 100 is assembled with the second clamping mechanism 70 using a motor mounting bracket or base 102.

The shutter mechanism assembly 90 is configured to receive the needle 16 end of the syringe assembly 10, and is the mechanism responsible for clamping and removing the needle 16 and/or cap 20 from the syringe assembly 10, while retaining the syringe hub 14 with the syringe assembly 10, and for releasing or otherwise depositing the needle 16 and/or cap 20 into the sharps container 40. While it is contemplated that the needle 16 is capable of removal from the syringe assembly 10 separately from the needle cap 20, the more likely scenario includes that the needle 16 is removed along with the needle cap 20. As contemplated herein and in an embodiment, to suggest that the cap 20 is removed inherently means that the needle 16 is also removed and/or that removal of the needle 16 includes removal of the cap 20, if attached.

Figure 11:
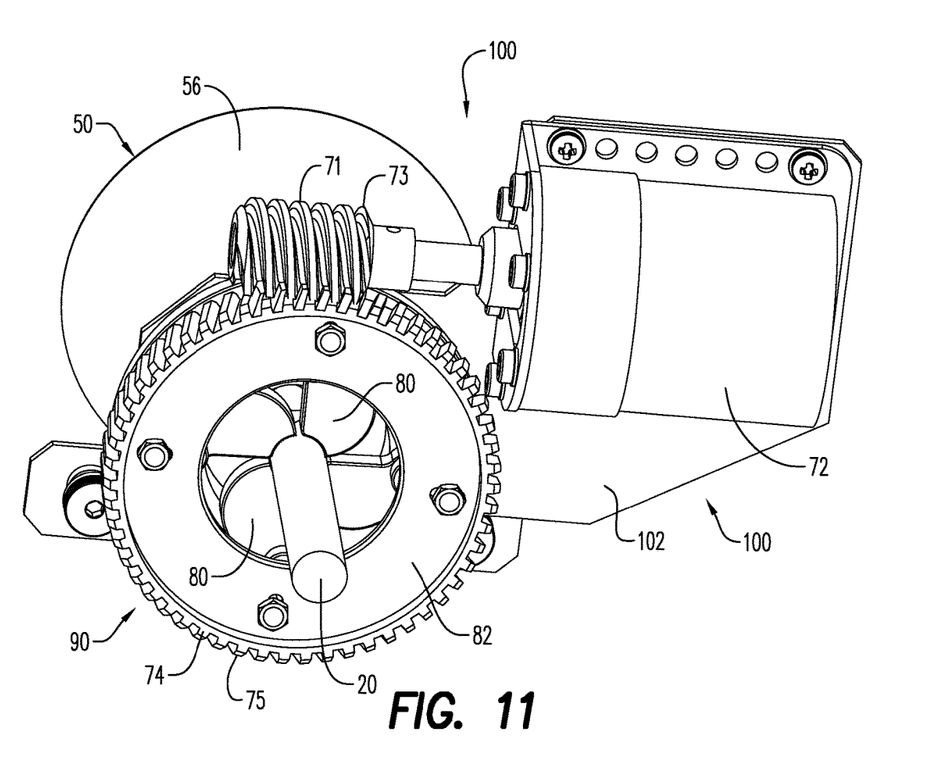
FIG. 11 is a perspective view of a motor, gear and second clamping mechanism according to an embodiment.
Figure 12A:
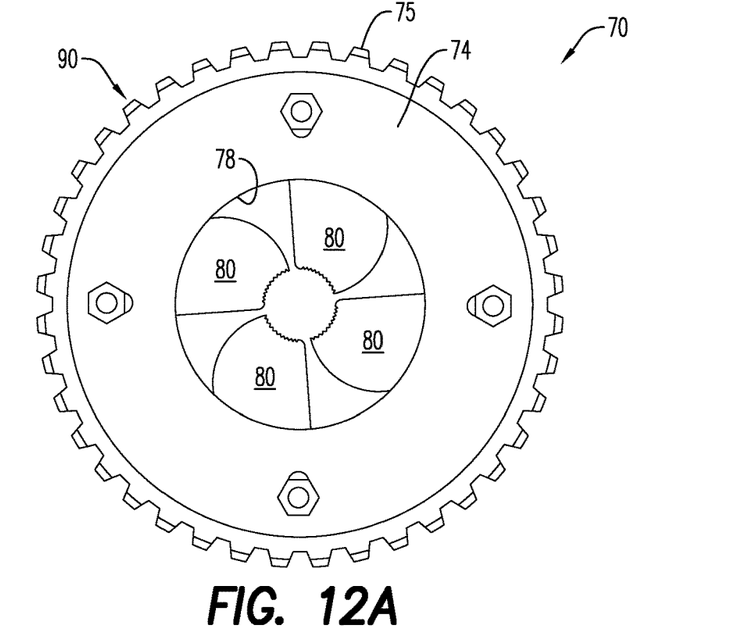
FIGS. 12a and 12b illustrate opposite sides of the second clamping mechanism of FIG. 11.
Figure 12B:
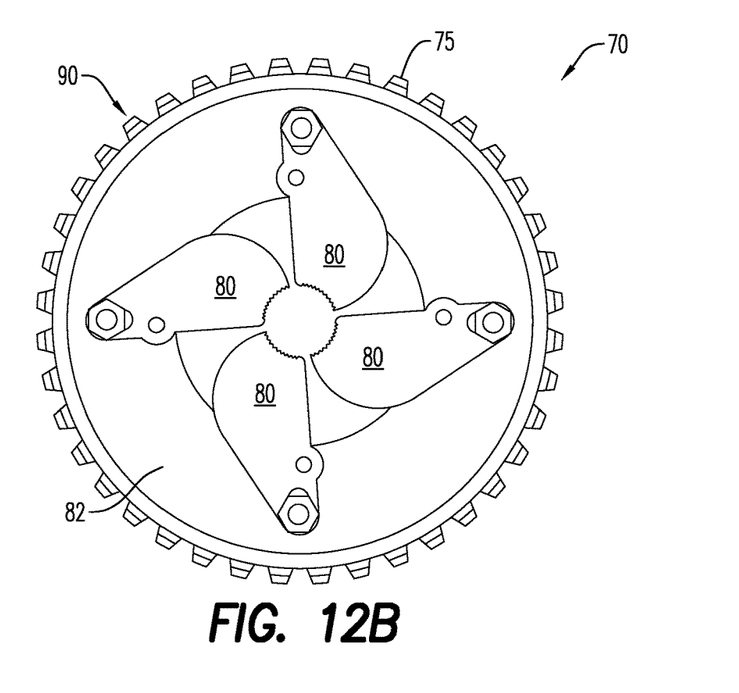
Figure 13:
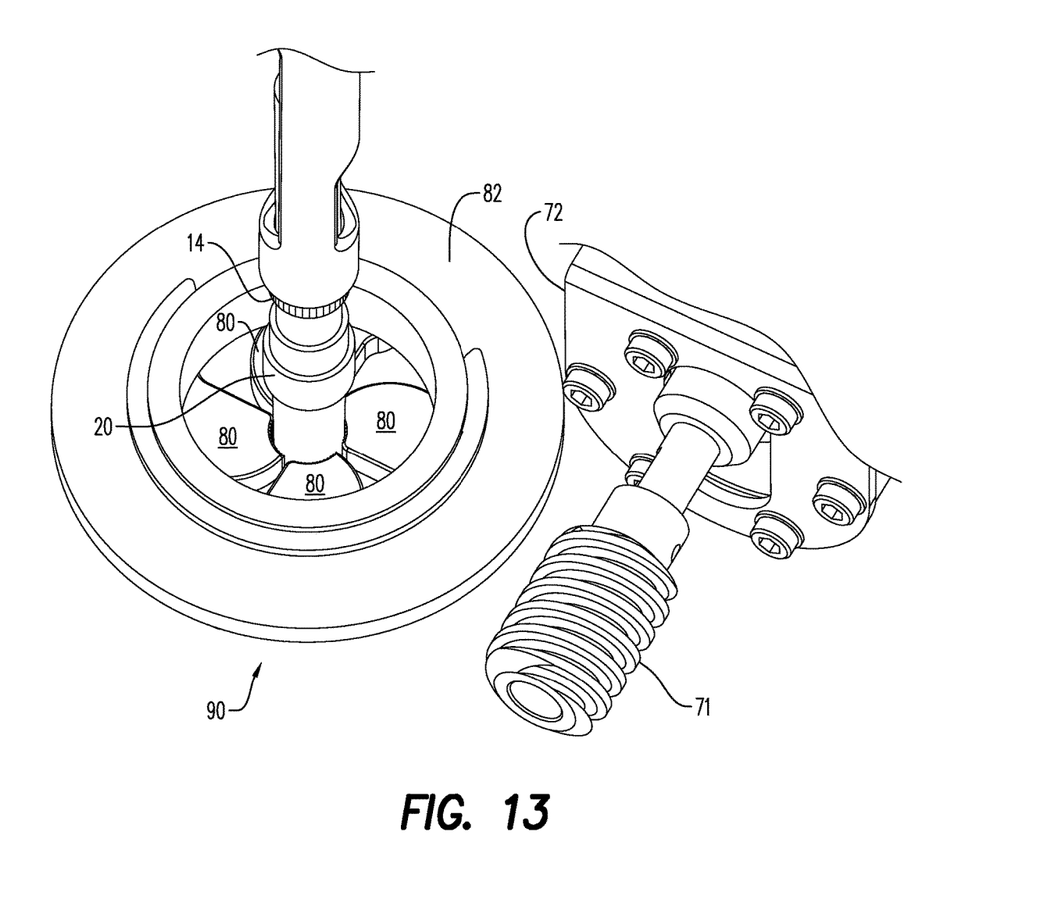
FIG. 13 is a partial perspective view of the needle handling apparatus according to an embodiment.

With reference to FIGS. 12a and 12b and in an embodiment, the shutter mechanism assembly 90 typically includes a gear plate 74, a backing plate 82 and a plurality of jaws or arms 80 sandwiched between the gear plate 74 and the backing plate 82. In an embodiment and as depicted in FIGS. 12a and 12b, the arms 80 are shaped like a lobster-claw. While four arms 80 are depicted herein, it would be understood that more or less arms 80 may be sufficient to perform the stated function, i.e. to grasp and hold the needle cap 20. For instance, the plurality of arms could include 2, 3, 4, 5, 6, 7, or more arms. The gear plate 74 typically includes a plurality of gear plate teeth 75 along an outer peripheral edge thereof, the gear plate teeth 75 configured to mesh with the worm gear 73 that is turned by the motor 72 of the motor/gear assembly 100 (see FIG. 11). As shown in FIG. 11, the gear 71 has been activated to turn the gear plate 74, which in turn pivots each of the plurality of arms 80 towards a center of the gear plate 74 and towards the inserted needle cap 20 and into contact with the needle cap 20 to grasp and/or hold the needle cap 20 in place. In this way, the needle cap 20 can be held or clamped with sufficient force that the healthcare professional can remove the syringe assembly 10 from the cap 20, one or more times to further inject the patient, and then to re-cap the needle 16, for as many times as deemed necessary. Although not shown, the arms 80, when positioned in a retracted or non-grasping position, would be either out of contact with the needle cap 20, or if contacting the needle cap 20, would not have sufficient force to grasp or hold the needle cap 20, allowing the needle cap 20 to move freely between ends of the arms 80.

Figure 6A:
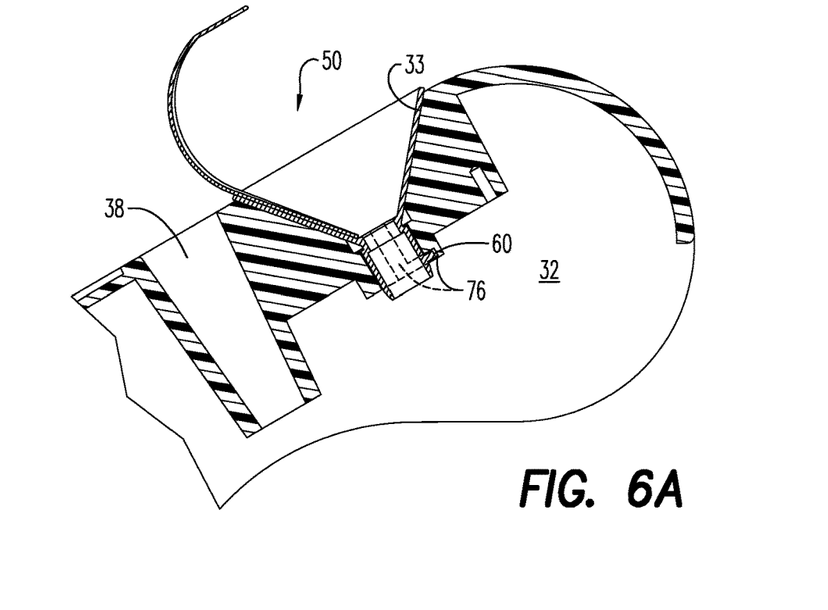
FIG. 6A is a cross-sectional cut-away view of a removable protective sleeve with sleeve locking mechanism of FIG. 4 according to an embodiment.

Turning again to FIGS. 6, 6A and 8, the channel 58 of the protective sleeve 50 may be further adapted to include a sleeve locking mechanism 60 along an outer surface thereof, and the outer surface of the channel 58 may further be configured to include an end portion 64 (see, in particular, FIGS. 6 and 6A), which is typically configured with a tapered outer surface. The end portion 64 of the channel 58 is configured to be received in an opening 78, which could be configured as a tapered slot as shown herein, of the shutter mechanism assembly 90, for instance. As depicted in an embodiment and with particular reference to FIG. 6A, the channel 58 of the funnel 50 is configured to be received within the opening 33 of the housing 32. In an embodiment, the opening 33 has the same general shape as the channel 58 of the funnel 50, including a recess or notch 76 to receive the sleeve locking mechanism 60. Thus, when the protective sleeve 50 is positioned in or connected to the shutter mechanism assembly 90, the sleeve locking mechanism 60 may be positioned within the recess 76 in the housing opening 33, and twisted into a locking position such that the sleeve 50 is only capable of slight movement (e.g. about 0.1 to 1.0 mm) in the direction of arrow F (FIG. 6), and does not move in a direction perpendicular the direction of arrow F. In an embodiment, movement of the sleeve 50 in the direction of arrow F automatically triggers activation of the clamping mechanisms described herein. When the end portion 64 is pressed into the tapered slot 78, an inner circumference of the first clamping mechanism 62 is reduced to grab and/or clamp the syringe hub 14 for the purpose of holding it in place when the seconding clamping mechanism 70 rotates to remove or extract the needle 16 and/or the needle cap 20, which is released into sharps container 42, while the syringe assembly 10 retains the syringe hub 14.

Once the dental procedure is complete, and the syringe assembly 10 is no longer needed for this patient, the second clamping mechanism 70 can be further actuated to twist the needle cap 20 to remove the cap 20 from the syringe assembly, typically along with the needle 16, while retaining the syringe hub 14 with the syringe assembly 10. With reference again to FIG. 6, upon completion of the dental procedure, the healthcare professional applies an additional force F to the syringe assembly 10, pushing the channel 58 of the sleeve 50 into the opening 78 formed in the shutter mechanism assembly 90, thus pinching the channel 58 to at least partially close the slotted opening 59. In an embodiment, the opening 78 is tapered to matingly interact with the tapered outer surface of the end portion 64 of the channel 58. Thus, the first clamping mechanism 62 tightens around the syringe hub 14 to retain it with the syringe assembly 10 and to hold it in place while the needle 16 and cap 20 are twisted off of the needle end 15 of the syringe hub. In an alternative embodiment, the first clamping mechanism 62 could be activated electronically rather than mechanically as set forth above. In other words, an electronic button or switch could be positioned on the control panel 44 for activation upon completion of the dental procedure, to electronically initiate removal of the needle 16 and cap 20 from the syringe assembly 10 while retaining the syringe hub 14 with the syringe assembly 10.

Figure 15:
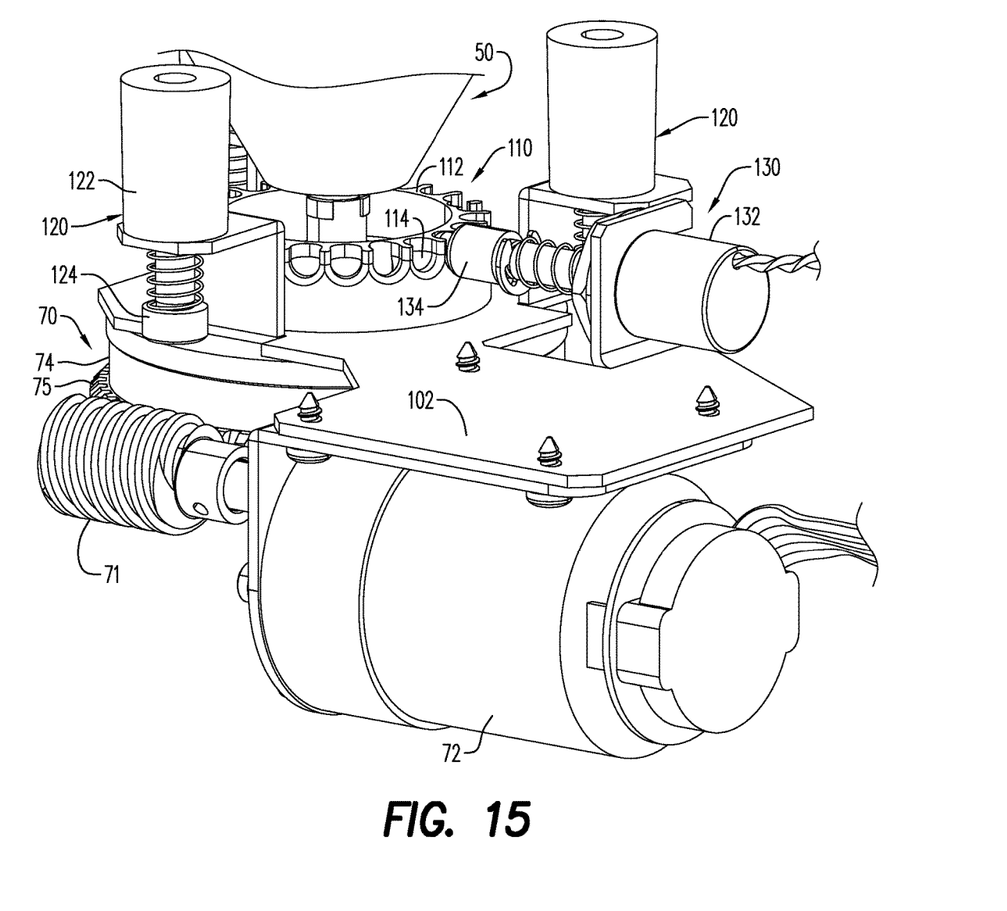
FIG. 15 is a perspective view of the needle containment device including a lock wheel, tension and wheel locking mechanism according to an embodiment.

With reference to FIG. 15 and in an embodiment, a lock wheel 110 is positioned in working relationship with the second clamping mechanism 70, and the lock wheel 110 includes a plurality of indentations 114 positioned along a peripheral edge 112 thereof. The lock wheel 110 is provided in an embodiment as a safety feature. In essence, the lock wheel 110 functions to lock the gear in position in order to prevent any "reverse rotation," (i.e., rotation in a direction opposite of the rotation required to unscrew the needle/cap), which could compromise the locking of the needle cap. In an embodiment, the locking wheel 110 is attached to the gear plate 74. The indentations 114 are configured for receiving a wheel locking pin 134 extending from an actuator 132 (typically a hydraulic or pneumatic valve) of a wheel locking mechanism 130. In an embodiment, the actuator 132 and wheel locking pin 134 are co-mounted on the motor mounting bracket 102, along with the motor/gear assembly 100. As depicted in FIG. 15, the motor/gear assembly 100 and the gear plate 74 are positioned on one side/surface of the mounting bracket 102, while the wheel locking mechanism 130 and the locking wheel 110 are positioned on an opposite side of the mounting bracket 102. Thus, although not shown, there is an orifice in the mounting bracket 102 for effecting connection of the locking wheel 110 to the gear plate 74. Additionally, it is possible to have extensions protruding from the mounting bracket 102 for ease of attachment of the various components.

As shown herein, the wheel locking pin 134 is capable of moving into and out of the wheel locking mechanism 130 to engage or disengage one of the indentations 114 to unlock or lock the lock wheel 110, respectively. The second clamping mechanism 70, may be energized by detecting a presence of the needle cap 20 within the needle containment device 30, and energizing the motor 72 to rotate the worm gear 73, allowing rotation of the gear 74 to move the arms 80 into grasping engagement with the needle cap 20. As an example, the needle cap 20 may be detected by a motion sensor, or may break a laser beam, (not shown) signaling the second clamping mechanism 70 to engage the needle cap 20. Once the needle cap 20 has been sufficiently grasped by the arms 80, the wheel locking mechanism 130 is activated (e.g. energized) to disengage the wheel locking pin 134 from the indentation 114 of the locking wheel 110, thus allowing both the second clamping mechanism 70 and the locking wheel 110 to rotate. The components will rotate a sufficient amount of cycles until the needle cap 20 is unscrewed and removed from the syringe assembly 10, (and in an embodiment, from the syringe hub 14).

During rotation and in an embodiment, the second clamping mechanism 70 is pushed away from the motor mounting bracket 102 while the arms 80 grasp the needle cap 20, via one or more tension mechanisms 120, which as depicted in FIG. 15, is attached to the mounting bracket 102. Since in an embodiment, the motor/gear assembly 100 is attached to the underside of the mounting bracket 102, the tension mechanism 120 functions to provide slight movement/motion to travel with the needle cap 20 when the needle cap 20 is disengaging. The tension mechanism 120 includes a tension actuator 122, and a tension arm 124 depending therefrom. In an embodiment, the tension mechanism 120 is spring loaded (×3) to offset the movement of the needle cap 20 while it is being disengaged (as it rotates clockwise it will be moving downward while the clamp jaws or arms 80 are engaged). In any case, the syringe assembly 10 remains stationary at all times. As depicted and in an embodiment, the plurality of tension mechanisms 120 are spaced equidistantly around the periphery of and capable of contact with an upper surface of the gear plate 74 to push the gear plate 74 away, while the arms 80 are grasping the needle cap 20, and to thus remove the needle cap 20.

After the needle cap 20 is thus removed, the wheel locking mechanism 130 is reactivated (e.g. de-energized) to return the wheel locking pin 134 into locking engagement with one of the indentations 114 of the locking wheel 110, to stop the locking wheel 110 from further rotation. The motor/gear assembly 100 is reactivated to retract the arms 80, thereby releasing the needle cap 20 (and needle 16) into the sharps container 42 (not shown).

The components and methods illustrated are not limited to the specific embodiments described herein, but rather, features illustrated or described as part of one embodiment can be used on or in conjunction with other embodiments to yield yet a further embodiment. It is intended that the machine and method include such modifications and variations. Further, steps described in the method may be utilized independently and separately from other steps described herein.

While the machine and method has been described with reference to specific embodiments, it will be understood by those skilled in the art that various changes may be made and equivalents may be substituted for elements thereof without departing from the scope contemplated. In addition, many modifications may be made to adapt a particular situation or material to the teachings found herein without departing from the essential scope thereof In this specification and the claims that follow, reference will be made to a number of terms that have the following meanings. The singular forms "a," "an" and "the" include plural referents unless the context clearly dictates otherwise. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. In some instances, the approximating language may correspond to the precision of an instrument for measuring the value. Terms such as "first," "second," "upper," "lower," etc. are used to identify one element from another, and unless otherwise specified are not meant to refer to a particular order or number or arrangement of elements. In other words, it is envisaged that multiple clamping devices are provided as necessary to conduct the method described herein.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of" Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

Advances in science and technology may make equivalents and substitutions possible that are not now contemplated by reason of the imprecision of language; these variations should be covered by the appended claims. This written description uses examples to disclose machine and method, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. A method of automatically removing a needle from a syringe hub and depositing the needle into a needle handling device, the method comprising:
    inserting at least a portion of a syringe assembly into the needle handling device, the syringe assembly comprising the needle and the syringe hub;
    activating the needle handling device to automatically remove the needle from the syringe hub; and
    depositing the needle into a removable sharps container while the syringe hub remains attached to the syringe assembly.

2. The method of claim 1, wherein removing the needle from the syringe hub comprises:
    clamping the syringe hub via a first clamping mechanism; and
    clamping the needle via a second clamping mechanism.

3. The method of claim 2, wherein removing the needle from the syringe hub further comprises:
    unscrewing the needle via the second clamping mechanism.

4. The method of claim 1, further comprising:
    clamping a needle cap via a second clamping mechanism, the needle cap covering the needle, the clamping of the needle cap sufficient to hold the needle cap while the syringe assembly is selectively removed for one or more needle re-capping events.

5. The method of claim 1, comprising:
    positioning the removable sharps container to receive the needle removed from the syringe hub.

6. The method of claim 1, further comprising:
    automatically detecting the insertion of the needle into the needle handling device and in response to automatically detecting the insertion, automatically activating removal of the needle from the syringe hub.

7. A reusable needle handling device configured for receiving at least a portion of a syringe assembly, the syringe assembly including at least a needle threadingly connected to a syringe hub, the reusable needle handling device comprising:
    a first clamping mechanism to clamp the syringe hub; and
    a second clamping mechanism including a shutter mechanism, wherein the shutter mechanism includes at least a gear plate, a backing plate, and a plurality of arms, wherein each of the arms is positioned between and pivotably connected to each of the gear plate and the backing plate and the gear plate is rotatable relative to the backing plate, wherein the plurality of arms are configured for clamping the needle and unscrewing the needle from the syringe hub when the gear plate is rotated relative to the backing plate.

8. The needle handling device of claim 7, further comprising;
    a removable sharps container positioned adjacent the needle handling device, wherein the second clamping mechanism releases the needle into the removable sharps container while the first clamping mechanism retains the syringe hub.

9. The needle handling device of claim 7, further comprising:
    a mechanism for automatically rotating the needle.

10. The needle handling device of claim 7, further comprising:
    a sensor to automatically detect an insertion of the needle into the needle handling device and in response to automatically detecting the insertion, automatically activating the second clamping mechanism to clamp the needle.

11. The needle handling device of claim 7, wherein the syringe assembly further comprises a needle cap, and wherein the plurality of arms are configured for clamping the needle cap when the gear plate is rotated relative to the backing plate.

12. The needle handling device of claim 11, wherein each of the plurality of arms are further configured to pivot toward an inserted needle cap and into contact with the inserted needle cap to grasp the inserted needle cap in place when the gear plate is rotated relative to the backing plate.

13. The needle handling device of claim 7, wherein the second clamping mechanism is assembled with a motor.

14. The needle handling device of claim 13, wherein the second clamping mechanism is assembled with the motor using a mounting bracket.

15. The needle handling device of claim 14, wherein the mounting bracket comprises a tension mechanism configured to offset movement of the needle while the needle is being unscrewed.

16. The needle handling device of claim 15, wherein the tension mechanism is spring loaded.

17. A reusable needle handling device comprising:
    a removable protective sleeve configured for receiving at least a portion of a syringe assembly, wherein the syringe assembly comprises a needle and a syringe hub, the needle being screwed onto the syringe hub;
    a first clamping mechanism to clamp the syringe hub;
    a second clamping mechanism to clamp the needle and to automatically remove the needle from the syringe hub; and
    a sensor to automatically detect an insertion of the needle into the needle handling device and in response to automatically detecting the insertion, automatically activating the second clamping mechanism to clamp the needle and remove the needle from the syringe hub.

18. The needle handling device of claim 17, further comprising:
    a removable sharps container positioned adjacent the needle handling device, wherein the second clamping mechanism releases the needle into the removable sharps container while the first clamping mechanism retains the syringe hub.

19. The needle handling device of claim 17, wherein the second clamping mechanism comprises:

a plurality of arms configured for the clamping of the needle.

\* \* \* \* \*